United States Patent
Grifka

[19]

[11] Patent Number: 5,810,752
[45] Date of Patent: Sep. 22, 1998

[54] KNEE JOINT ORTHOSIS

[75] Inventor: Joachim Grifka, Bochum, Germany

[73] Assignee: Otto Bock Orthopaedische Industrie Besitz- und Verwaltungs KG, Duderstadt, Germany

[21] Appl. No.: 52,737

[22] Filed: Apr. 27, 1993

[30] Foreign Application Priority Data

Apr. 29, 1992 [EP] European Pat. Off. ............ 92107261

[51] Int. Cl.$^6$ ..................................................... A61F 5/00
[52] U.S. Cl. ............................................... 602/16; 602/26
[58] Field of Search .................. 602/5, 16, 26, 602/20, 23; 128/870, 882

[56] References Cited

U.S. PATENT DOCUMENTS

| | | |
|---|---|---|
| 2,460,895 | 2/1949 | Meany . |
| 4,632,097 | 12/1986 | Brooks . |
| 4,776,326 | 10/1988 | Young et al. ........................ 602/26 X |
| 4,793,333 | 12/1988 | Marquette ................................ 602/26 |
| 4,966,133 | 10/1990 | Kausek ................................ 602/26 X |
| 5,018,514 | 5/1991 | Grood et al. ....................... 602/26 X |
| 5,133,341 | 7/1992 | Singer et al. ....................... 602/26 X |
| 5,207,637 | 5/1993 | Janke et al. ............................ 602/26 |

FOREIGN PATENT DOCUMENTS

| | | |
|---|---|---|
| 0 356 623 | 3/1990 | European Pat. Off. . |
| 2 441 382 | 6/1980 | France . |
| 8 517 061 | 10/1985 | Germany . |
| 4 013 693 | 8/1991 | Germany . |
| 1454461 | 1/1989 | U.S.S.R. ................................. 602/16 |

*Primary Examiner*—Linda C. Dvorak
*Attorney, Agent, or Firm*—Foley & Lardner

[57] ABSTRACT

A knee joint orthosis having a thigh part, which is to be attached to the thigh by harnesses or the like, a lower leg part, which is likewise to be attached to the lower leg by harnesses or the like, and two joint splints which are located laterally opposite each other and connect the two leg parts with each other in an articulated manner. To improve the function as well as the construction design, according to the invention, each of the two joint splints is constructed so that it is telescopically adjustable in length, and is coupled at its upper end to the thigh part and at its lower end to the lower leg part, and a device is provided which effects a dorsalization of the lower leg by the retroposition of the joint splints.

19 Claims, 2 Drawing Sheets

KNEE JOINT ORTHOSIS

BACKGROUND OF THE INVENTION

The invention relates to an orthosis (that is, a support or brace for weak or ineffective joints or muscles), and more particularly to a knee joint orthosis, having a thigh part which is to be fixed to the thigh by means of harnesses or the like, a lower leg part, which is likewise to be fixed to the lower leg by means of harnesses or the like, and two joint splints which are located laterally opposite each other and which connect the two leg parts with each other in an articulated manner.

An embodiment of this nature is evident from DE 40 13 693 C2. This previously known knee joint orthosis comprises two joint splints, which can be attached laterally opposite each other by means of harnesses to the thigh and lower leg, and each of which splints is formed of a thigh splint and a lower leg splint which are connected to each other via a hinge. Straps, which are adjustable lengthwise, are attached to the free ends of the joint splints, two on the front side of the leg, where they are arranged in parallel, and two on the rear side of the leg, where they are arranged to cross over each other. Two ribbon-shaped cross connectors, which possess guidance slits through which the parallel straps extend, are attached to the thigh splints as well as to the lower leg splints.

The aim of so-called functional orthoses of this nature is to reduce the joint mechanics, which are different and individually variable on the internal and external sides of the knee joint, to a biomechanical simplification, which is based on the course of the anterior and posterior crucial ligament, and finds its expression in the production of specific joints. It is not only the influence of remaining ligament structures which is ignored by this approach. The different movement sequences on the inner and outer sides of the knee joint are also not taken into consideration; the knee joint is forcibly guided. The fact that the movement sequences of the articulated orthosis and of the knee joint can never be matched with each other is shown by shearing movements of the orthosis parts, during which the leverage forces of the splint arms on the one hand affect the knee joint movement and on the other provoke regions of chafing on the skin. The bindings which are commonly used to adapt the splint parts on the thigh and the lower leg lead to additional constrictions and to restriction of movement, in particular in the region of the popliteal fossa.

Disadvantages of the previously known knee joint orthoses include the fitting of the orthosis, which is very awkward and complicated, and the heavy weight of some of the appliances.

SUMMARY OF THE INVENTION

The object on which the invention is based is to improve the knee joint orthosis described in the introduction, both in its function and from the point of view of its construction.

This object is achieved according to the invention by each of the two joint splints being constructed so that it is telescopically alterable lengthwise, and being coupled by its upper end to the thigh part and by its lower end to the lower leg part, and by providing a device which effects a dorsalization of the lower leg by means of the retroposition of the joint splints.

To achieve the foregoing object and in accordance with the purpose of the invention, as embodied and broadly described herein, a knee joint orthosis comprises a thigh part which is adapted to be attached to a thigh by a harness; a lower leg part which is adapted to be attached to a lower leg by a harness; and two joint splints which are located laterally opposite each other and connect the thigh part and the lower leg part with each other in an articulated manner; wherein each of the two joint splints is constructed so that it is telescopically adjustable in length, and is coupled at its upper end to the thigh part and at its lower end to the lower leg part; and wherein a device is provided for effecting a dorsalization of the lower leg by the retroposition of the joint splints.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

The drawing diagrammatically represents an embodiment of the invention which serves as an example.

DETAILED DESCRIPTION OF THE PREFERRED EMBODIMENTS

Figure 1:
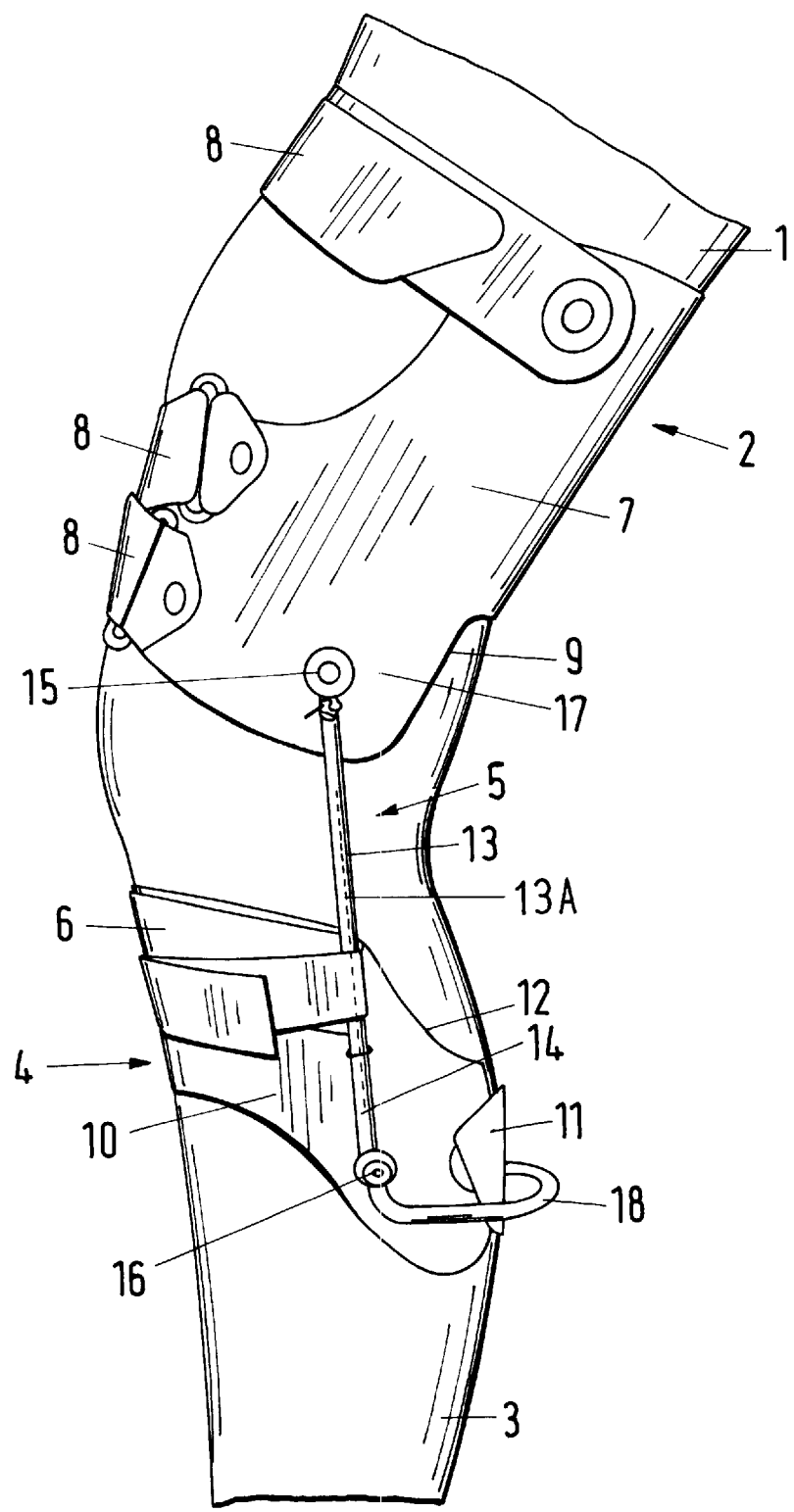
FIG. 1 shows, in a lateral aspect, a knee joint orthosis attached to a leg.

It is thus to be regarded as an important feature of the orthosis according to the invention that a mechanical joint which imitates the individual knee joint mechanism is no longer provided. Rather, the knee joint mechanism is given full freedom to allow it to carry out the physiological movement in an unimpeded manner. The respective center of movement, together with the course of the joint axis, which also varies laterally, can be located between the coupling points of the joint splints in accordance with the individual anatomical circumstances. By means of the connection between the thigh part and the lower leg part of the orthosis, rising up or slipping and chafing as a result of an autonomous orthosis joint mechanism is avoided.

According to the invention, it is expedient if the device effecting the dorsalization of the lower leg by means of the retroposition of the joint splints is a ventral elastic tension binding which is taken round the lateral joint splints. The tension binding can, according to the invention, comprise only one single binding which is taken round both the joint splints and is alterable lengthwise, which binding, as a result of its ventral arrangement, leaves the region of the popliteal fossa completely free, and therefore permits powerful flexion.

In principle, other embodiments of the said device are conceivable. For example, the tension binding can be attached to the joint splints in each case via an element, for example an extension spring, which is extensible lengthwise. It is also possible for the device to be constructed as a spring-loaded pivoted lever whose fulcrum lies in the region of the lower coupling point of the joint splint, and whose free lever end is attached to the joint splint from behind at a point which is at some distance from the fulcrum.

According to the invention, the two coupling points of a joint splint are arranged in such a way that when the leg is extended, the joint splint, in accordance with the individual leg axis, is approximately perpendicular and approximately in the center of the sagittal plane of the leg, while with increasing flexion of the knee, the joint splints move behind the fulcrum of the knee. This is the case since a false positioning of the sagittal leg axis is also, corresponding to the individual characteristics, compensated for due to the rotatable coupling of the joint splint at the proximal point in all three directions in space, and by the separate length adjustment of the joint splint. The particular feature of these joint splints is that they are independent of the anatomical and functional turning mechanism of the knee joint. In principle, they could indeed lie behind the fulcrum of the knee in their initial position, an arrangement which has not been realized solely for reasons of practicability.

The fitting of the orthosis, in particular, is found to be particularly simple and reliable if the thigh part and the lower leg part is in each case formed by a shell which to a large degree encompasses the leg (upper shell, lower shell).

To permit a very powerful flexion of the knee, until the thigh and lower leg come in contact with each other, it is expedient for each shell to have a piece cut out dorsally in the region of the popliteal fossa.

To prevent the upper shell slipping downwards because of the conical anatomy of the thigh, it is advantageous if the upper shell has condyle bedding on its inner surface above the inside thigh condyle. This condyle bedding can also be constructed as a separate, individually locatable, truss pad, which can, for example, be attached at the desired point by means of a VELCRO fastener. However, there is also the possibility of constructing the relevant interior region of the upper shell to be deformable, so that it can adapt to the individual circumstances. A water or gas filling, which can also be constructed to be self-regulating, can be proposed for this purpose.

It is likewise advantageous for securing the position of the shells if they are in each case provided with an inner lining.

To increase the deformation rigidity of the lower leg part in relation to the thigh part, it is advantageous if the two lower coupling points of the joint splints are connected to each other via a dorsal hoop. This hoop can be taken around externally at a good clearance around the dorsal region of the lower shell, or be integrated directly into the lower shell.

Further features of the invention are set out below, and are illustrated in more detail, in conjunction with further advantages of the invention, using an embodiment as an example.

Figure 2:
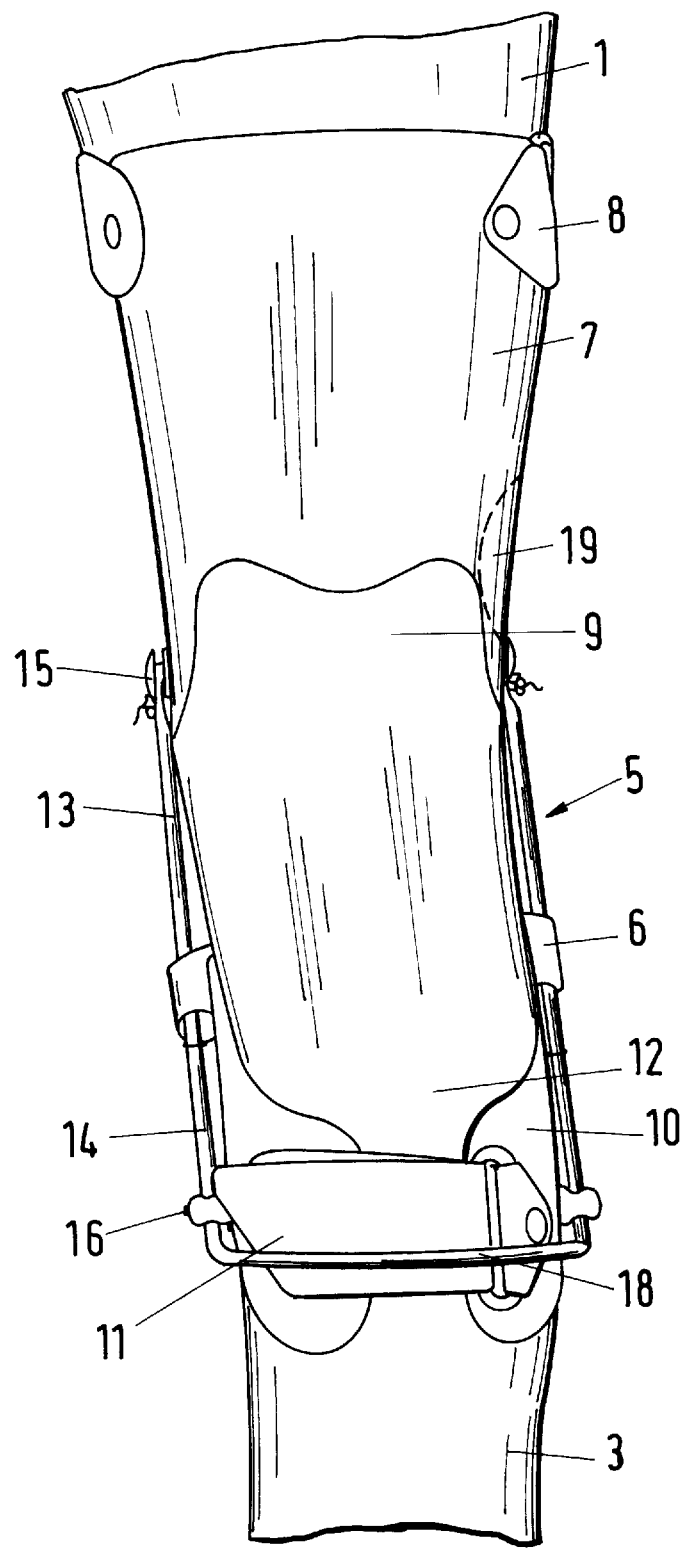
FIG. 2 shows the representation according to FIG. 1 in a posterior aspect.

The knee joint orthosis which is represented in FIGS. 1 and 2 comprises a thigh part 2 which is to be attached to the thigh 1, a lower leg part 4, which is to be attached to the lower leg 3, and two joint splints 5 situated laterally opposite each other and connecting the two leg parts 2, 4 with each other in an articulated manner. An elastic tension binding 6 is also provided which is taken ventrally around the joint splints 5 as a cross connector.

The thigh part 2 is formed by an upper shell 7 which to a large extent encompasses the thigh 1, which shell is open ventrally, and in this region can be closed by VELCRO (i.e., loop and hook) fasteners 8, and dorsally in the region of the popliteal fossa has a cutout 9 which leaves this region free.

The lower leg part 4 is likewise formed by a lower shell 10 which to a large extent encompasses the lower leg 3, which shell is open dorsally and can be closed here by means of a VELCRO fastener 11, and dorsally in the region of the popliteal fossa has a cutout 12.

According to the invention, each of the two joint splints 5 is constructed so that its length can be adjusted telescopically. In the embodiment example which is presented, each joint splint 5 comprises an upper telescope tube 13 and a lower telescope rod 14 which is guided inside it, which parts can be connected to each other by means or an inner elastic lining, which is not represented in detail in the drawing and which it is also possible to replace with a stretch stop. An elastic device permanently limits movement of the joint splint 5 in a direction of its shortening. The upper end of the telescope tube 13 is coupled to the upper shell 7 via a coupling point 15, while, correspondingly, the lower end of the lower telescope rod 14 is coupled to the lower shell 10 via a coupling point 16. While the connection of the two coupling points 15, 16, formed by the coupling splint 5, is alterable lengthwise, it is otherwise constituted to be rigid. The upper coupling point 15 of the inner coupling splint 5 is located in the condyle region 17 of the upper shell 7, while the lower coupling point 16 is located in the calf region of the lower shell 10. In this way, the two coupling points 15, 16 of each joint splint 5 are so arranged that, when the leg is extended, the joint splint 5 is approximately perpendicular and approximately in the center of the sagittal plane of the leg, while, with increasing flexion of the knee, the joint splints 5 move behind the knee fulcrum.

The two lower coupling points 16 of the joint splints 5 are connected to each other via a dorsal hoop 18.

The tension binding 6 comprises a single tension strap taken around the two joint splints 5, the two free ends of which strap can be connected with each other in a lengthwise-adjustable manner, for example by means of a VELCRO fastener.

As shown in FIG. 2, the upper shell 7 possesses a condyle bedding 19 on its inner surface above the inside thigh condyle, which bedding can be constructed as a separate truss pad, which can be individually locatable, for example by means of a VELCRO fastener, or is formed by a deformable region which can be filled with a gas or fluid, and is optionally constructed to be self-regulating. This region can also be formed by silicone paste. Whatever the case, the condyle bedding serves as a support, and thus as an aid in achieving improved fixation of the upper shell 7 which, because of the conical anatomy of the thigh 1, has a tendency to slip downwards. In association with this, the condyle bedding is so arranged that it changes shape to conform to the anatomy of the thigh condyle region.

To prevent a shift in position, or to secure the position, of the shells 7, 10, the latter preferably possess an inner lining, which is not shown in more detail in the drawing and which can be composed of an anti-slip material.

The tension binding 6 is constructed in such a manner, or is adjusted in such a manner, that, while it is relatively slack when the leg is extended, it leads, as knee flexion increases, to increasing dorsalization of the lower leg, i.e., to an increasing posteriorly-directed traction which is applied to the lower leg.

The dorsal cutouts 9, 12 in the shells 7, 10 form anatomically appropriate leg cutouts, as a result of which pressure sites in the popliteal fossa are avoided. In this way, maximum flexion is possible, since neither tension bindings nor regions of the shell are present in the vicinity of the popliteal fossa.

The knee joint orthosis according to the invention has no influence on the individual, physiological rolling-gliding mechanism of the knee joint, and therefore does not lead to disintegration of the natural movement sequence. In preserving the original mechanics, it is only the protection of the head of the tibia against a forward displacement, in association with reduced muscular activity, which is impeded. When standing with the leg extended, the rear musculature of the thigh essentially prevents displacement of the tibia head forwards, while the patellar ligament is without tension. When the knee joint is extended, the ventral tension binding provided according to the invention exerts a moderate traction, and thereby ensures a good fit for the orthosis, and develops increasing traction in association with further flexion of the joint.

The knee joint orthosis according to the invention thus possesses no mechanical joint which attempts to imitate the individual knee joint mechanics. The respective movement center, together with the course of the joint axis, which also varies laterally, can be located between the coupling points of the joint splints in accordance with the individual anatomical relationships. By means of this connection between thigh part and lower leg part 2, 4, a rising up or slipping and chafing, as the result of autonomous orthosis joint mechanics, is avoided. The two parts 2, 4, which per se are independent of each other, are located securely on the leg. There is only a slight shift in position due to unavoidable volume changes in the thigh and lower leg as the result of muscular contraction. The special arrangement of the two joint splints 5 ensures that constancy of support is maintained during the through movement.

In principle, the above-described restraining mechanism for a knee joint orthosis, without a fixed joint movement axis, can also be employed for other orthotic joint appliances, for example as a shoulder joint orthosis.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A knee joint orthosis comprising:
   a thigh part which is adapted to be attached to a thigh by a harness;
   a lower leg part which is adapted to be attached to a lower leg by a harness; and
   two rigid joint splints, that is, a first lateral joint splint and a second lateral joint splint, which are located laterally opposite each other and connect the thigh part and the lower leg part with each other in an articulated manner;
   wherein each of the two joint splints is constructed so that it is telescopically adjustable in length, and is coupled at its upper end to the thigh part via an upper pivotal point and at its lower end to the lower leg part via a lower pivotal point; the upper pivotal points and the lower pivotal points defining the only axes of rotation of the orthosis; and
   wherein a device is provided for effecting a dorsalization of the lower leg.

2. The knee joint orthosis as claimed in claim 1, wherein the device is adapted to effect dorsalization of the lower leg by retroposition of the joint splints.

3. The knee joint orthosis as claimed in claim 2, wherein the device is a ventral elastic tension binding which is taken around the first and second lateral joint splints.

4. The knee joint orthosis as claimed in claim 3, wherein the tension binding is one tension strap which is taken around the joint splints and is adjustable lengthwise.

5. The knee joint orthosis as claimed in claim 1, wherein two coupling points of one joint splint are so arranged that when a leg is extended the joint splint, in accordance with an individual leg axis, is located approximately perpendicularly and approximately in the center of a sagittal plane of the leg, while with increasing flexion of a knee the joint splints move behind the knee fulcrum.

6. The knee joint orthosis as claimed in claim 1, wherein each joint splint comprises two telescopic bars which are telescopically introduced into each other.

7. The knee joint orthosis as claimed in claim 1, wherein the thigh part and the lower leg part are each formed by an upper shell and a lower shell, respectively, which substantially encompasses the leg.

8. The knee joint orthosis as claimed in claim 7, wherein each shell possesses a cutout dorsally in a region of a popliteal fossa.

9. The knee joint orthosis as claimed in claim 8, wherein the upper shell can be closed ventrally by a hook and loop fastener.

10. The knee joint orthosis as claimed in claim 9, wherein the lower shell can be closed dorsally by a hook and loop fastener.

11. The knee joint orthosis as claimed in claim 7, wherein the upper pivotal point of the first joint splint is located in a condyle region of the upper shell.

12. The knee joint orthosis as claimed in claim 11, wherein the lower pivotal point of the two joint splints is located in a calf region of the lower shell.

13. The knee joint orthosis as claimed in claim 7, wherein the upper shell possesses a condyle bedding on its inner surface above an inside thigh condyle.

14. The knee joint orthosis as claimed in claim 13, wherein the condyle bedding is constructed as a separate, individually locatable, truss pad.

15. The knee joint orthosis as claimed in claim 13, wherein the condyle bedding is formed by a deformable region.

16. The knee joint orthosis as claimed in claim 7, wherein each shell possesses an inner lining for securing its position.

17. The knee joint orthosis as claimed in claim 1, wherein the lower pivotal points of the two joint splints are connected to each other by a dorsal hoop.

18. The knee joint orthosis as claimed in claim 1, further comprising an elastic device which permanently limits movement of the two rigid joint splints in a direction of its shortening.

19. A knee joint orthosis comprising:
   a thigh part which is adapted to be attached to a thigh by a harness;
   a lower leg part which is adapted to be attached to a lower leg by a harness; and
   two joint splints which are located laterally opposite each other and connect the thigh part and the lower leg part with each other in an articulated manner;
   wherein each of the two joint splints is constructed so that it is telescopically adjustable in length, and is coupled at its upper end to the thigh part via an upper pivotal point and at its lower end to the lower leg part;
   wherein a device is provided for effecting a dorsalization of the lower leg; and
   wherein an elastic device permanently limits movement of the joint splint in a direction of its shortening.

* * * * *